(12) United States Patent
Walker

(10) Patent No.: US 7,406,899 B2
(45) Date of Patent: Aug. 5, 2008

(54) AUTOMATIC FEED MEDICAL SCREWDRIVER

(76) Inventor: Douglas D. Walker, 1833 Portola Rd., Suite K, Ventura, CA (US) 93003

( * ) Notice: Subject to any disclaimer, the term of this patent is extended or adjusted under 35 U.S.C. 154(b) by 0 days.

(21) Appl. No.: 11/506,489

(22) Filed: Aug. 18, 2006

(65) Prior Publication Data
US 2008/0016989 A1   Jan. 24, 2008

Related U.S. Application Data

(63) Continuation of application No. 11/492,536, filed on Jul. 24, 2006, now abandoned.

(51) Int. Cl.
   *B25B 23/04* (2006.01)
   *B25B 23/08* (2006.01)
(52) U.S. Cl. .......................... 81/434; 81/451
(58) Field of Classification Search .................. 81/434, 81/436, 438, 435, 451, 461, 13, 55, 452, 81/125; 411/406, 407
See application file for complete search history.

(56) References Cited

U.S. PATENT DOCUMENTS

| 1,330,098 | A | * | 2/1920 | Smith ........................... 81/461 |
|---|---|---|---|---|
| 2,304,704 | A | * | 12/1942 | O'Leary ...................... 411/406 |
| 3,946,926 | A | | 3/1976 | Willis |
| 4,018,334 | A | | 4/1977 | Lejdegard |
| 4,269,246 | A | | 5/1981 | Larson et al. |
| 4,408,877 | A | | 10/1983 | Lindmo et al. |
| 4,480,514 | A | * | 11/1984 | Ponziani ...................... 81/461 |
| 4,930,630 | A | | 6/1990 | Habermehl |
| 5,469,767 | A | | 11/1995 | Habermehl |
| 5,509,768 | A | | 4/1996 | Hon |
| 5,522,687 | A | | 6/1996 | Chen |
| 5,544,746 | A | | 8/1996 | Dohi |
| 5,562,547 | A | * | 10/1996 | Borzone ...................... 411/407 |
| 5,570,618 | A | * | 11/1996 | Habermehl et al. ........... 81/434 |
| 5,590,574 | A | | 1/1997 | Lide |
| 5,622,024 | A | | 4/1997 | Habermehl |
| 5,758,768 | A | | 6/1998 | Habermehl |
| 5,775,514 | A | | 7/1998 | Lin |
| 5,779,420 | A | | 7/1998 | Huang |
| 5,788,445 | A | | 8/1998 | Huang |
| 5,803,691 | A | | 9/1998 | Huang |
| 5,931,298 | A | | 8/1999 | Huang |
| 5,984,096 | A | | 11/1999 | Shinjo |
| 6,761,268 | B2 | | 7/2004 | Shinjo |
| 6,948,408 | B1 | * | 9/2005 | Lee .............................. 81/436 |
| 7,231,854 | B2 | * | 6/2007 | Kikuchi ....................... 81/434 |
| 2006/0086214 | A1 | * | 4/2006 | Smed ........................... 81/461 |

\* cited by examiner

*Primary Examiner*—Hadi Shakeri
(74) *Attorney, Agent, or Firm*—Koppel, Patrick, Heybl & Dawson; Michael J. Ram

(57) ABSTRACT

A fastener placement system for placement of screws into bone structure during a medical procedure comprises a power driven screw driver, a fastener carrier system with a series of fasteners temporarily attached thereto and an elongated band structure carried by the fastener carrier system for positioning and advancing the individual fasteners of the series of medical fasteners in a controlled manner to a position to receive a driving tip on the powered screw driver. The head of the fastener and the tip of the screw driver have complementary structures which allow the screw head to be simultaneously grasped by the driver tip and the fastener to be driven in a rotary manner for placement into the bone structure.

20 Claims, 16 Drawing Sheets

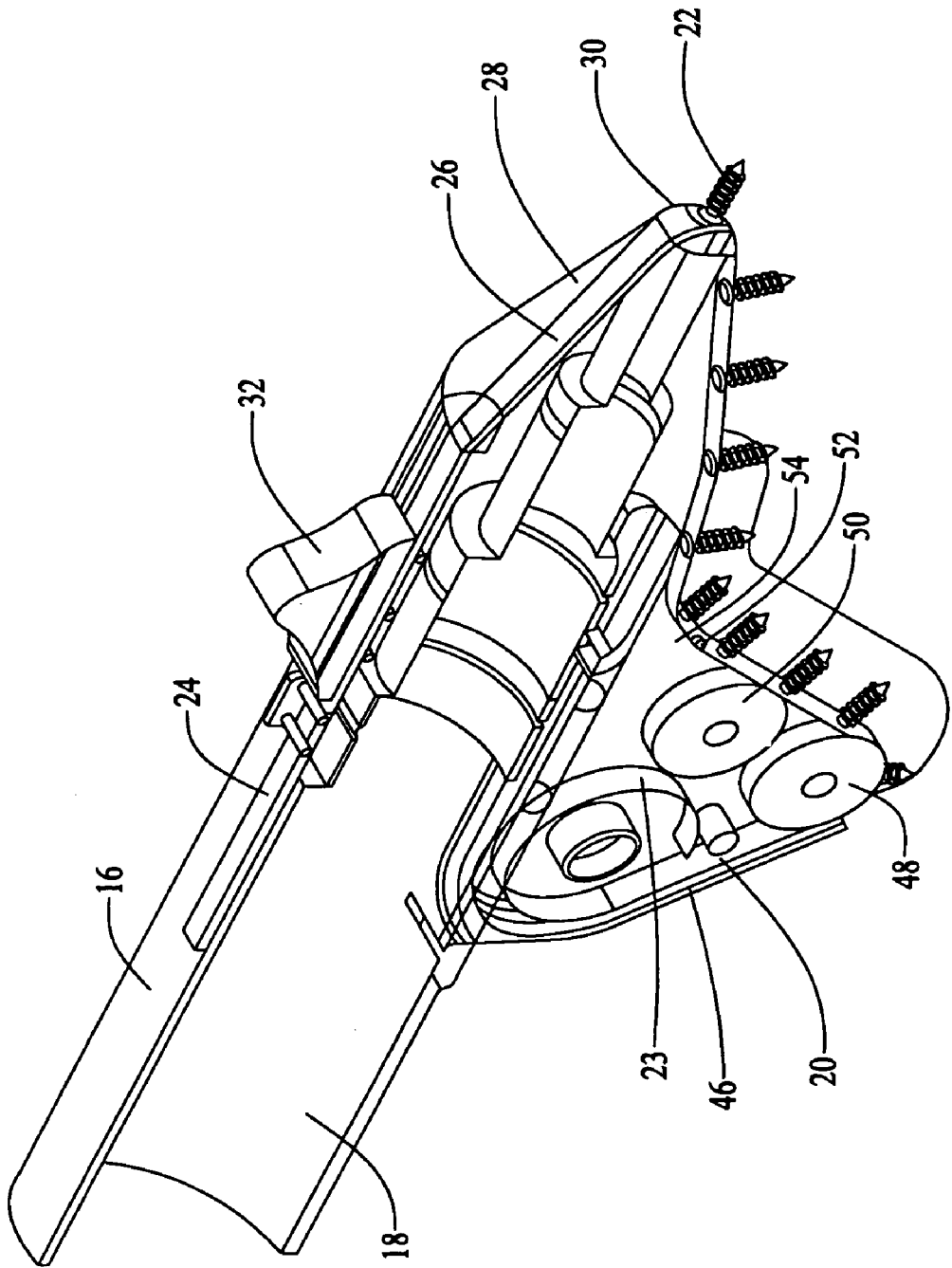

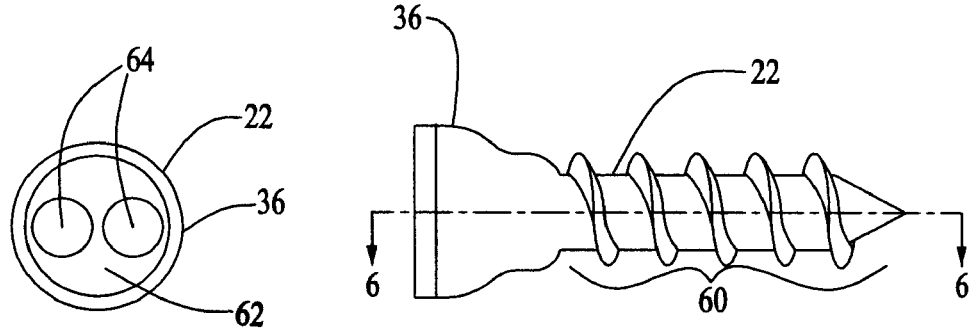
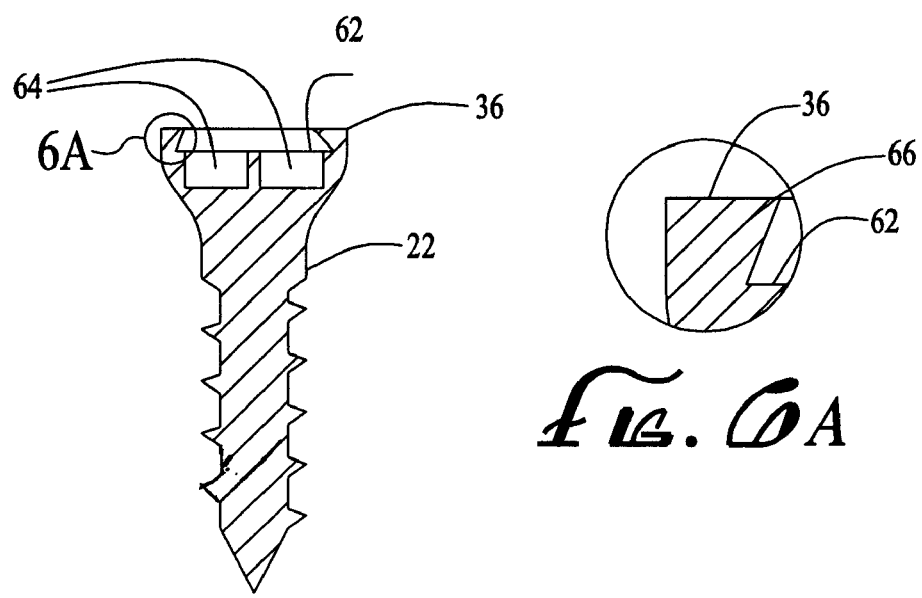

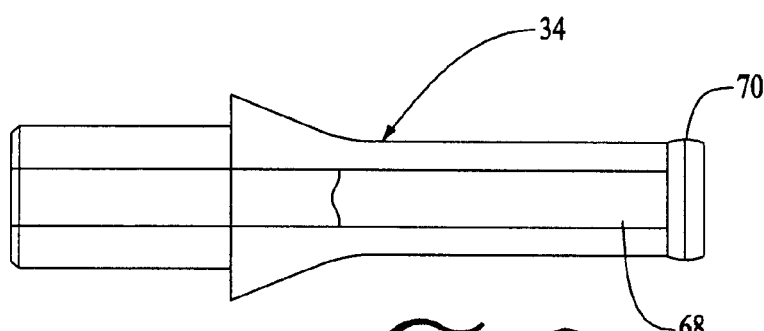
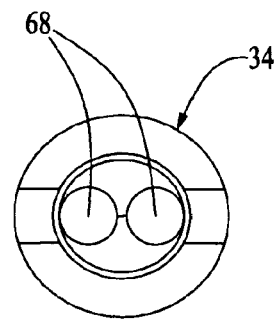
fig. 8
fig. 9
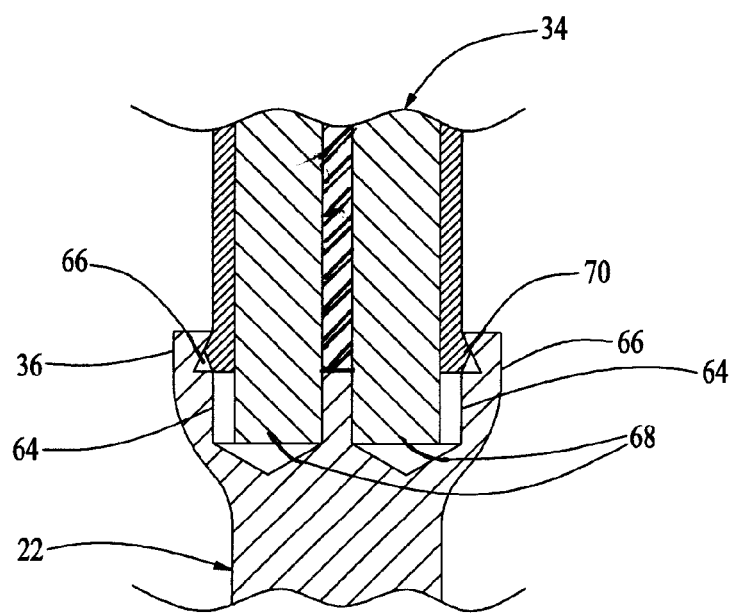
fig. 30

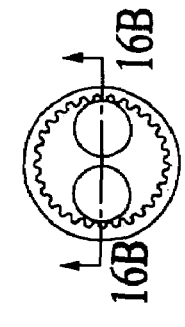
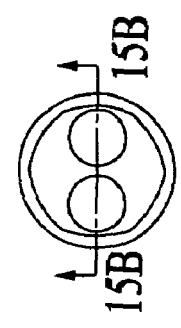
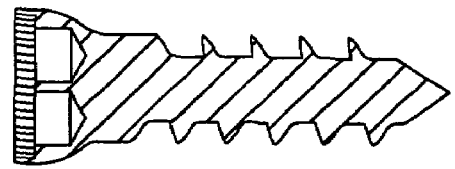
fig. 13A   fig. 14A   fig. 15A   fig. 16A
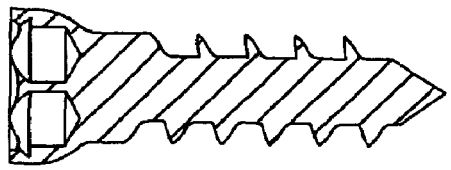
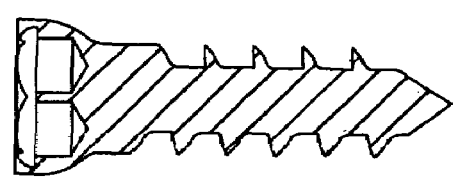
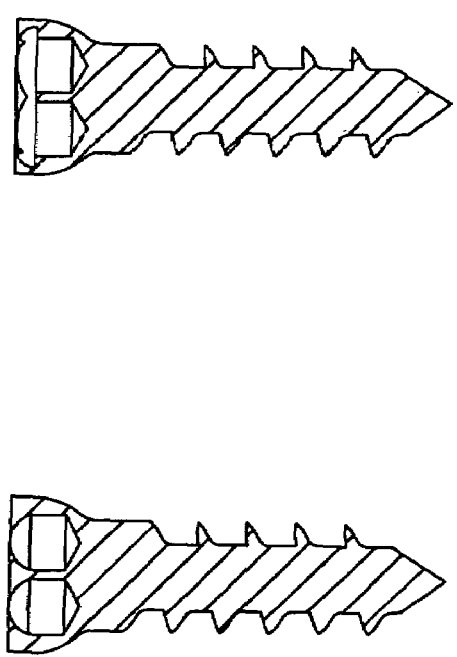
fig. 13B   fig. 14B   fig. 15B   fig. 16B

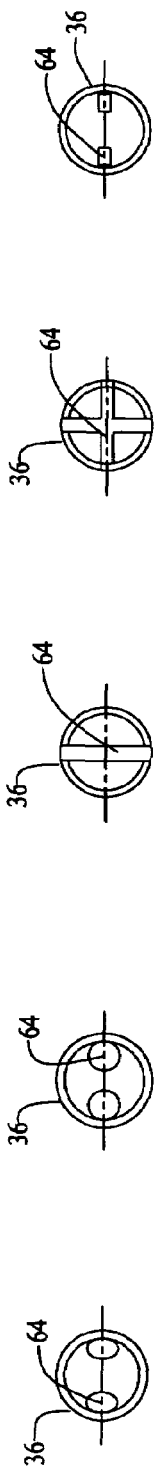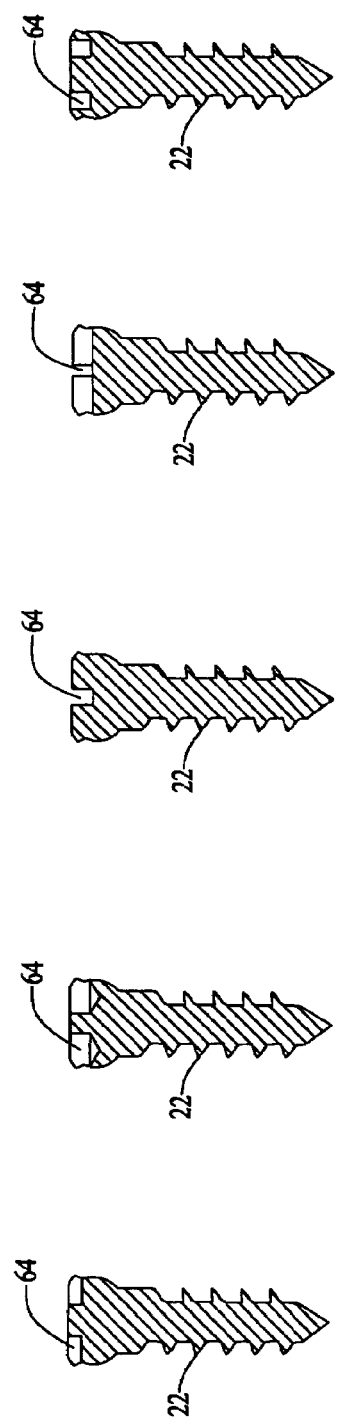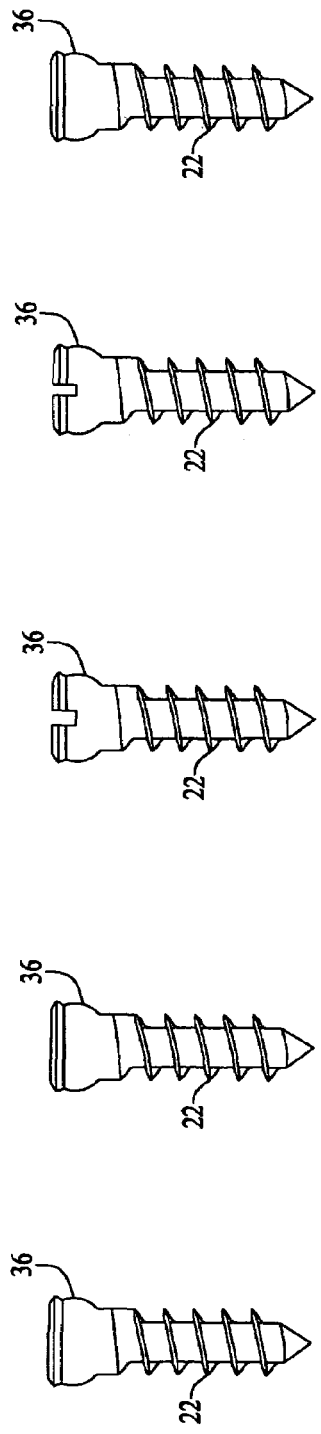

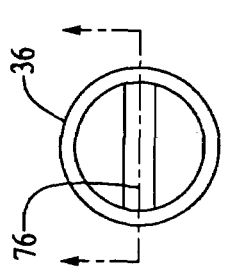
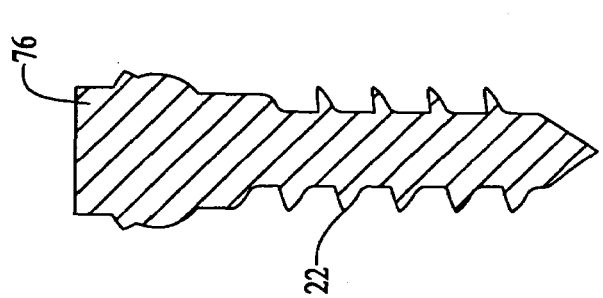
Fig. 23A  Fig. 23B
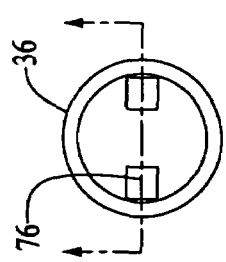
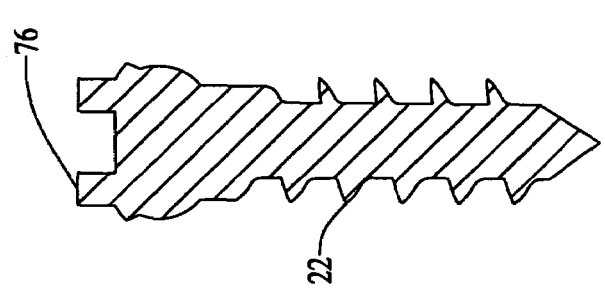
Fig. 24A  Fig. 24B
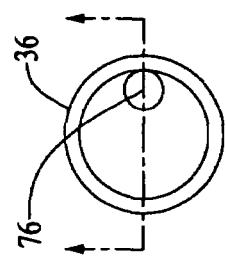
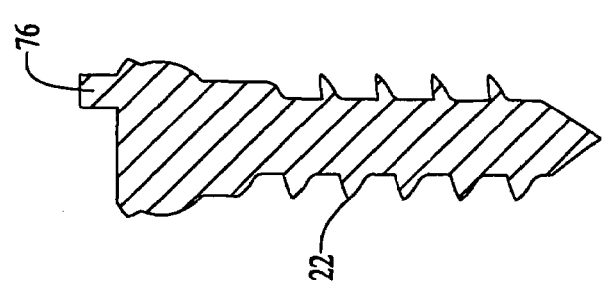
Fig. 25A  Fig. 25B
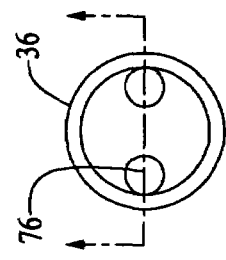
Fig. 26A  Fig. 26B

AUTOMATIC FEED MEDICAL SCREWDRIVER

This is a Continuation of U.S. patent application Ser. No. 11/492,536, filed Jul. 24, 2006 now abandoned.

The present invention is generally directed to a fastener and drive system comprising a driving tool and fasteners fed from a cartridge removeably attached to the driving tool including a feed system to position the fastener adjacent the active driving portion of the drive system. More specifically, the fastener and drive system is designed for placing screw fasteners into bones during a medical procedure and particularly for the placement of very small fasteners in cranial maxillofacial procedures and reconstruction of bone supported anatomical features.

BACKGROUND

Surgical reconstruction of hard tissue, such as the placement of prosthetics, the repositioning and attachment of fractured bones and the addition of metallic support plates to repaired bone typically require the placement of fasteners, which may be adhesives, mechanical devices, or combinations thereof. In many instances the fastening system includes screws, which may have special thread and head designs adapted for the particular application or the placement system. These screws are often very small in size and therefore difficult to handle, position and thread into the underlying structure and can easily be dropped into the surgical cavity if they are being manually manipulated.

Systems comprise manual screw drivers or, more recently, cordless, battery powered drivers, to transmit a rotational driving force to screws, which may have specialized heads to match the driver tips. Because a typical procedure may require placement of numerous screws (20-60) the powered drivers are now preferred. A typical power driver is a reusable pencil grip instrument with a replaceable, single use, sterile, disposable battery pack. However, hospital personnel must still perform the tedious task of attaching each screw to the tip of the screwdriver or into a retaining structure on the tip and then handing it to the surgeon or manually loading a feeding system adapted to place the screw in front of the driver tip. The screw head has a recessed structure, such as a slot or a recessed geometric structure for example, cruciform, Phillips, square, hexagonal or exalobe shaped holes, for torque transmission from a matching structure on the tip of the driver. For torque transmission and to limit the tip from disengaging from the structure in the screw head the tolerances of the fit between the tip and the screw head construction are minimal and in some instances tapered to provide secure engagement (U.S. Pat. No. 4,269,246 to Larson et al.)

There are numerous publications and patents which show devices that relate to the field of the invention. They are directed to the placement of, or automatic delivery of, fasteners to a particular location and systems for driving the fasteners. The following are merely representative of the art; there are others which are primarily repetitive of those discussed herein. Many are for industrial applications and can not meet the needs of a surgeon for use in an enclosed, sterile environment and do not lend themselves to automatic one hand operation. Systems for delivering a fastener to the operative, rotating tip of a screw driver include:

a) Non-Banded Delivery—U.S. Pat. No. 3,946,926 to Willis is an example of a pneumatic or strictly mechanical delivery of fasteners from a hopper. U.S. Pat. No. 4,408,877 to Lindmo et al. appears to cover loose screws fed along a track disposed in front of the screwdriver tip.

b) Stacked Fasteners—U.S. Pat. No. 5,590,574 to Lide is an example of a system that provides a linear arrangement of fasteners stacked head to tail inside the screwdriver.

c) Vertical Band—There are numerous patents to systems in which the fastener (nail or screw) lies across the face of a band and are attached to the band by notches or loops extending from the surface of the band. Alternatively the band may have a thickness so that the fastener can be inserted in a hole which extends through the band from one edge to a parallel opposite edge, for example, U.S. Pat. Nos. 5,758,768, 5,622,024, 5,469,767, and 4,930,630 to Habermehl as well as numerous other Habermehl patents. However, they all appear to use a band which attaches to the side of the fastener and which places the band in a plane coextensive with the axis of the screwdriver.

d) Horizontal Band—There are numerous patents that are directed to systems in which the screw is placed through a hole in the surface of the band with the band resting somewhere along the length of the shank of the screw or just below the head of the screw. These include U.S. patents to Chen (U.S. Pat. No. 5,522,687), Dohi (U.S. Pat. No. 5,544,746), Hon (U.S. Pat. No. 5,509,768), Huang (U.S. Pat. Nos. 5,931,298, 5,803,691, 5,788,445, 5,779,420), Lejdegard (U.S. Pat. No. 4,018,334), Lin (U.S. Pat. No. 5,775,514), and Shinjo (U.S. Pat. Nos. 5,984,096 and 6,761,268) all of which show various band designs which include extensions created from or formed below the surface of the band designed to grip the shaft of the screw.

Other patents are directed to the surgical fasteners and the design of the head of the fastener and drivers constructed to work with these fasteners or hold the fastener during the placement procedure. None of these patents include automatic delivery of the fasteners.

These prior devices do not provide the ease of operation and the ability to continuously and rapidly place numerous screws into the bone structure while minimizing the risk of loss of the screws during the procedure and the amount of time necessary to prepare the tool and the fasteners for use in the surgical procedure.

SUMMARY

A fastener, automatic delivery system for the fastener and a drive system, preferably powered by replaceable or rechargeable batteries which provide automated and continuous delivery and placement of the fasteners from a reloadable cartridge is shown.

BRIEF DESCRIPTION OF THE DRAWINGS

FIG. 4 is a perspective cutaway side view of the embodiment of FIG. 2 with screw fasteners placed in a band.

FIG. 5 is a side view of a first embodiment of a screw fastener for use in the fastener placement system.

FIG. 6 is a cross sectional view of the screw of FIG. 5 taken along line 6-6 of FIG. 5.

FIG. 6a is an enlarge view of the circled portion of FIG. 6.

FIG. 7 is a top view of the screw of FIG. 5 showing a first embodiment of structure in the screw head to receive a matching driver tip.

FIG. 8 is a side view of a driver tip designed to interact with the screw head embodiment of FIG. 7.

FIG. 9 is an end view of the driver tip of FIG. 8.

FIGS. 13a and 13b, 14a and 14b, 15a and 15b, and 16a and 16b show several additional embodiments of screw head constructions which provide structure within the screw head for grasping the fastener.

FIGS. 17a, b and c, 18a, b and c, 19a, b and c, 20a, b and c, and 21a, b and c are top, longitudinal cross sections and side views respectively of five embodiments of different hole structure in the head of the fastener as well as an external taper for external grasping of the fastener.

FIGS. 23a and b, 24a and b, 25a and b, and 26a and b are top and cross-sectional views respectively of further embodiments of the fastener including extensions from the head of the fastener in place of holes in the head.

FIG. 30 is a cutaway side view of the driver tip inserted into the head of the fastener of FIG. 5.

DETAILED DESCRIPTION

Figure 1:
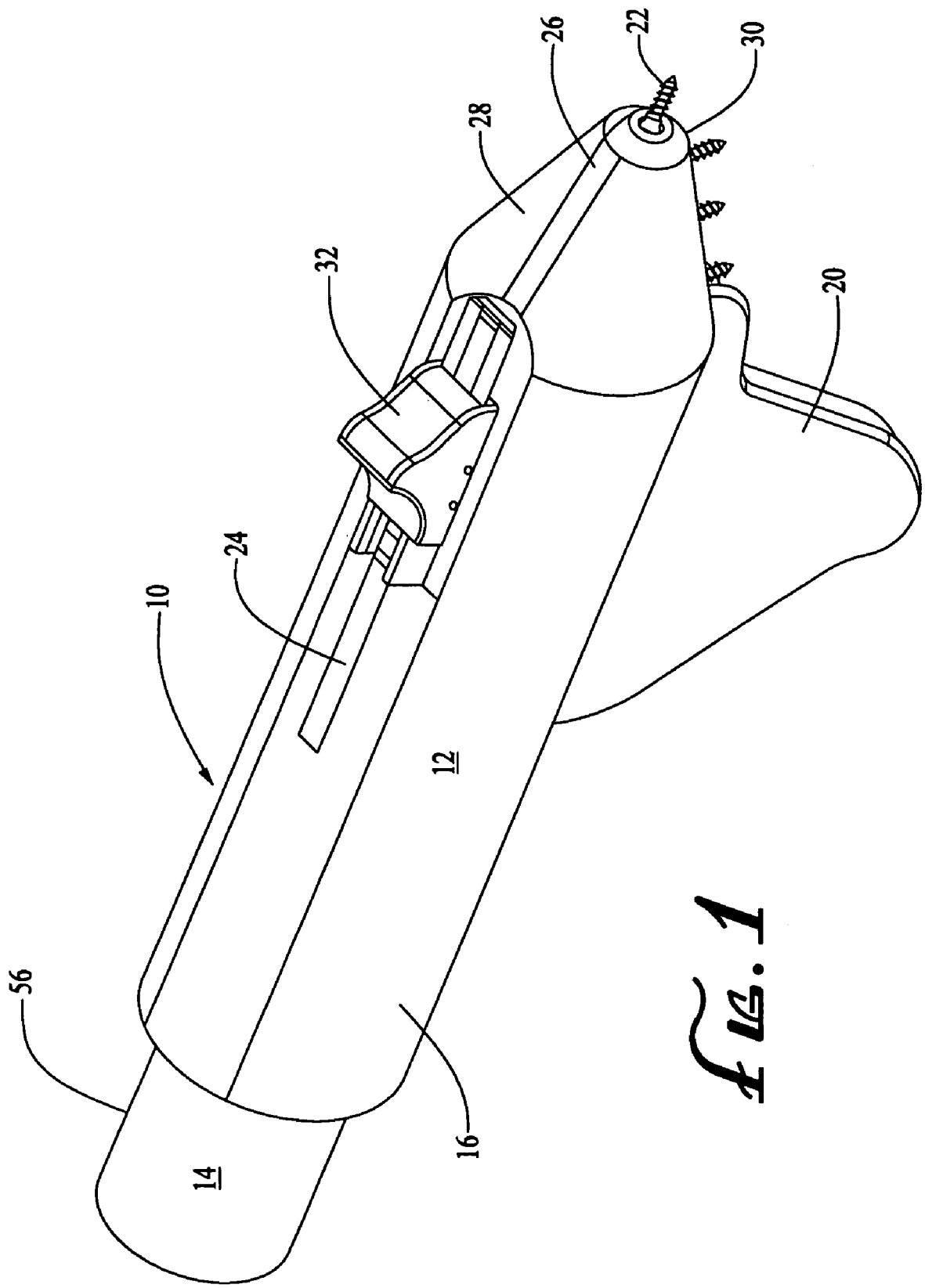
FIG. 1 is a perspective side view of a first embodiment of a fastener placement system incorporating features of the invention.

The fastener and driver disclosed herein, referred to in combination as a fastener system, is primarily intended for use in medical procedures which require the placement of small surgical screws, such as would be used in a cranial maxillo-facial procedures, prosthetic or an orthopedic procedure, which are automatically positioned and held in front of the tip of the screwdriver so that multiple screws can be placed in a serial manner by a one hand operation.

The fastener system includes an automatic finger activated driver having a tip which rotates around its central, longitudinal axis by an electrical drive means, such as rechargeable or replaceable batteries. While less preferred, the driver may alternatively be driven by external AC or DC power sources, or pneumatic or hydraulic drives. As a still further alternative gas cylinders inserted in the driver handle instead of batteries can be used to provide a replaceable or rechargeable drive system. As a still further alternative, the rotating tip can be driven by a negative pressure provided by an external vacuum source.

A feature of the system described herein is a fastener head construction and a driver tip configuration which allows the driver tip to be inserted into a depression in the head of the fastener or grasp the outer edge of the head, while at the same time separating the fastener from a carrier strip. This eliminates the task of manually mounting the fastener on the driver tip. The fastener can then be readily transported to the surgical placement site without fear of dropping the fastener and driven into the bone at the surgical placement site. The driver tip is then retracted, leaving the fastener in place in the bone and a subsequent fastener automatically moves into position in front of the driver tip to repeat the procedure.

A preferred embodiment uses a replaceable cartridge which includes an elongated band with multiple fasteners inserted centrally along the length of the band. The fasteners are held in the band by structure integral with the edges of holes in the band, the structure gripping the edge of the head of the fastener. However, other band structures or different retaining structures can be used to hold and place the fasteners in front of the driver tip. Still further, different means, such as a hopper containing fasteners can be used to funnel individual fasteners, one at a time, to a point in front of the driver tip where they are temporarily held until the driver tip locks into or onto the fastener head.

One skilled in the art, based on the disclosure set forth herein, can design other techniques to carry the fastener to a point in front of the driver tip for placement of the tip in the fastener head ready for driving into the surgical site.

In a first embodiment multiple screws are temporarily attached along the length of a band. The screw delivery system includes a removable and replaceable cartridge structure to enclose the band of screws and a track for the band of screws to travel along for placement in front of a screw driver tip. Each successive screw on the band is serially positioned in front of the tip of the screw driver tip. A trigger mechanism causes the band to move forward in front of the tip, placing the fastener in the right position to be engaged by the driver tip. The driver tip includes an enlarged portion which is inserted into the head of the screw or around the head of the screw so that when the screw is separated from the band the screw is retained on the tip by interlocking structures. Moving the tip forward engages the screw head, separates the screw head from the band, inserts pins on the tip or other geometric shapes into or around matching shapes in the fastener head, and provides rotary motion to the screw so that it can be driven into a target surface. This is accomplished by rotating the tip within the driver while the screw driver handle is held fixed (not rotated).

Figure 2:
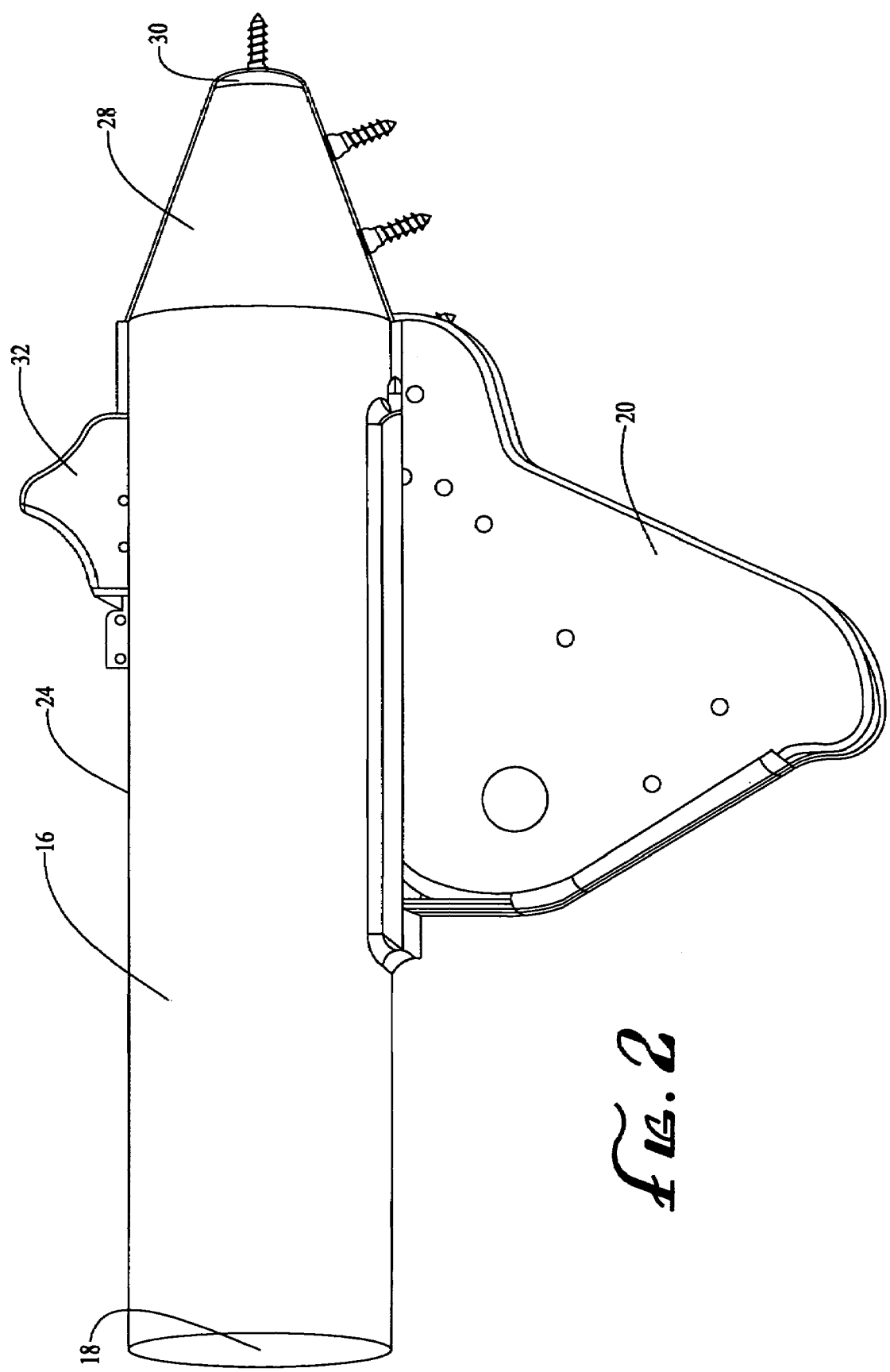
FIG. 2 is a side view of the screw delivery portion of the a fastener placement system of FIG. 1
Figure 3:
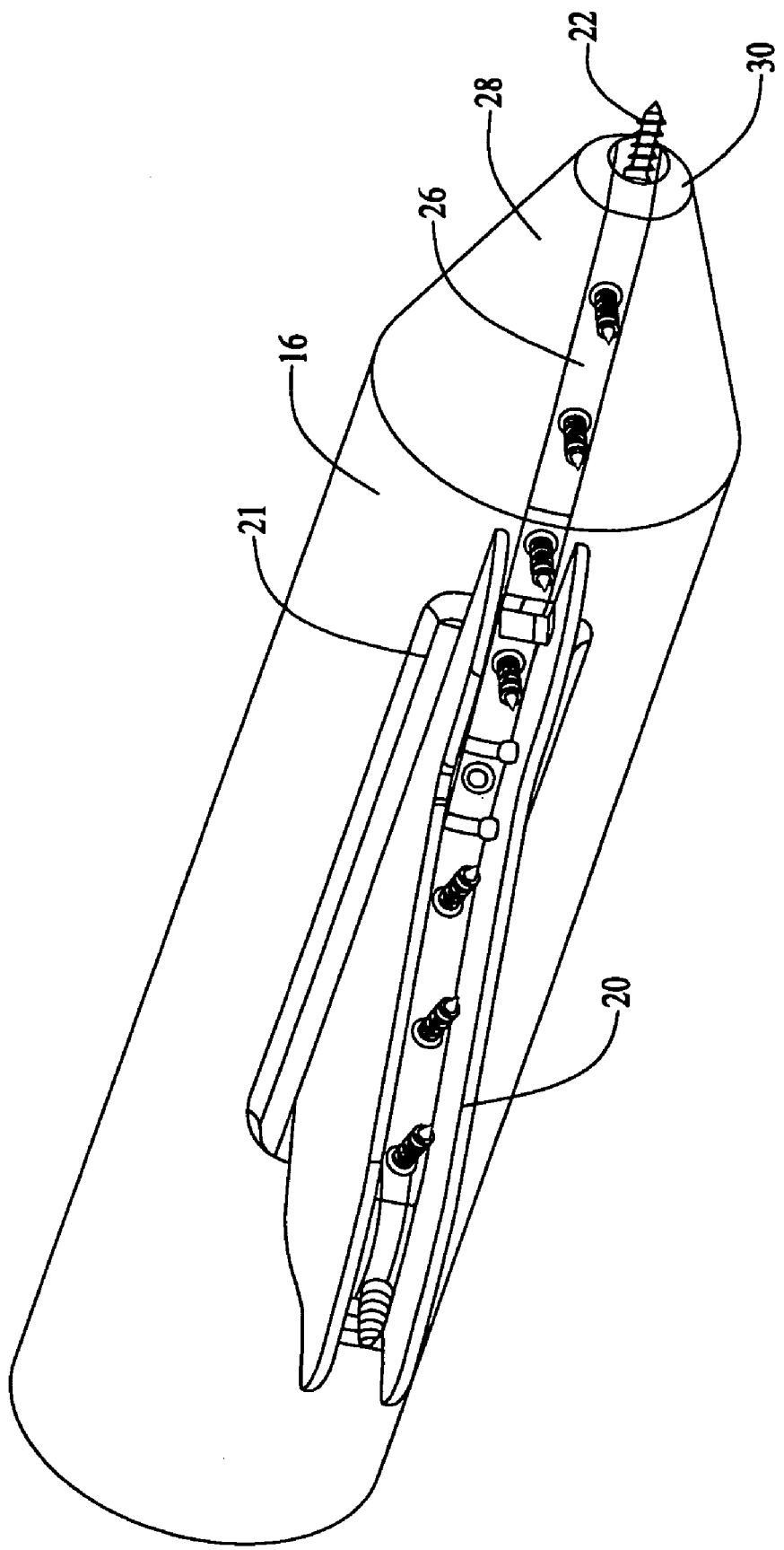
FIG. 3 is a perspective view of the lower side of the embodiment of FIG. 2 showing the fasteners in a carrying strip.

A perspective side view of a first embodiment of a fastener placement system 10, comprising a screw delivery portion 12 and a driver assembly 14 is shown in FIG. 1. The screw delivery portion 12, as best shown in FIGS. 2-4, comprises a cylindrical shell 16 (shown in FIGS. 13 and 14) which has a central, longitudinal opening 18 designed to receive and retain the driver assembly 14. A removable cartridge 20 carrying fasteners 22 is attached to a receiving track 21 on the lower surface of the cylindrical shell 16. The cartridge walls are preferably transparent so the user can see the quantity of fasteners remaining in the cartridge. The removable cartridge 20 is preloaded with a moveable strip 26 which carries the fasteners 22. Upon assembly for use the moveable strip 26 is extended from the removable cartridge 20 along the front portion 28 of the cylindrical shell 16, across the tip 30 of the shell 16 and rearwardly across the upper region of the front portion 28 where it is moveably connected to a trigger 32.

Figure 10:
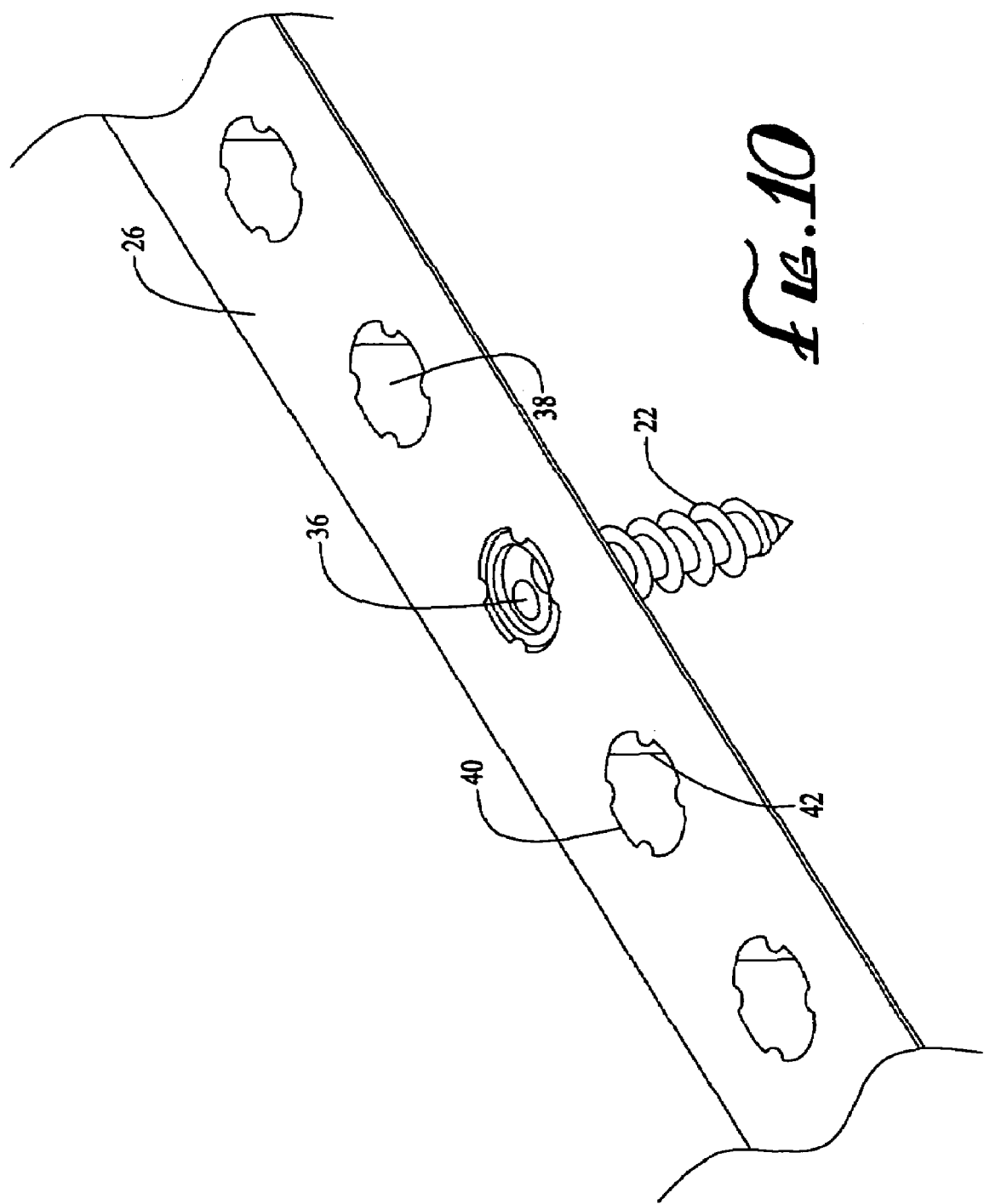
FIG. 10 is a top perspective view of the screw of FIG. 5 mounted in a first embodiment of a screw feeding band.

As shown in FIGS. 3 and 4, the fasteners 22 are temporarily and removeably attached to the elongated band or strip 26 such as shown in FIG. 10. The strip extends rearwardly beyond the last fastener 22 to provide a tail 23 for extending into the cartridge 20. A leading end 24 of the strip 26 extends forward from the front most fastener so that the strip 26 can be engaged with the under side of the trigger 32. In a preferred embodiment at least 10 fasteners 22 are attached and evenly spaced along the central portion of the strip 26. The attachment must be such that the fasteners 22 will remain in position on the strip 26 through assembly, packaging and transportation of the removable cartridge 20, installation of the cartridge 20 onto the cylindrical shell 16 and placement of the loaded strip across the tip 30 as well as movement across the front portion 28 of the cylindrical shell 16. The attachment must also be sufficient so that the driver tip 34 can engage with the head 36 of the fastener as the driver tip 34 is advanced forward. However, the temporary connection between the fastener 22 and the moveable strip 26 must also be readily disrupted thereafter by the further forward movement of the driver tip 34, the fastener 22 now temporarily and removeably carried by the driver tip 34. Typically, the fastener 22 is held in the strip 26 by a friction fit and/or horizontal or vertical extensions from the edge of mounting holes 38. Alternatively, a biocompatible glue or adhesive (not shown) could be used to temporarily secure the fastener 22 to the band 26.

Figure 11:
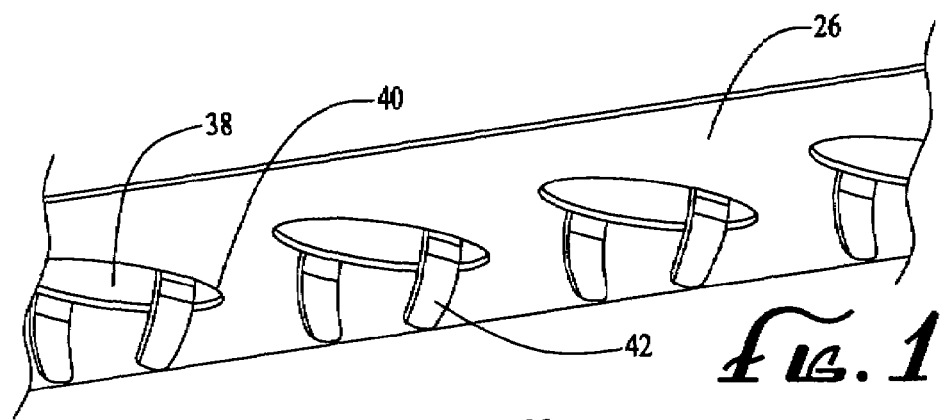
FIG. 11 is a bottom perspective view of the band of FIG. 10.
Figure 12A:
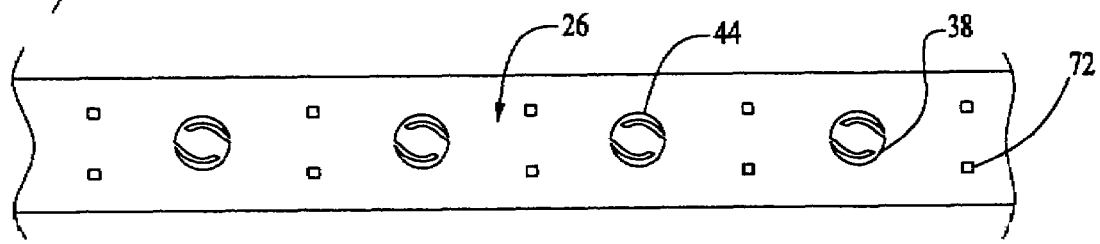
FIGS. 12a-12d show several embodiments of screw retaining configurations as part of holes in a screw feeding band.
Figure 12B:
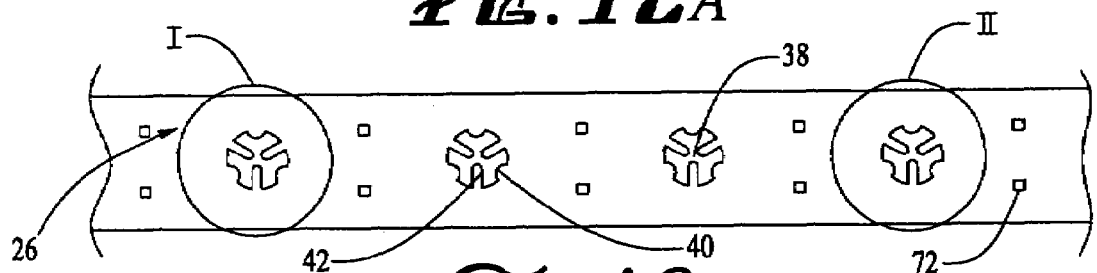
Figure 12C:
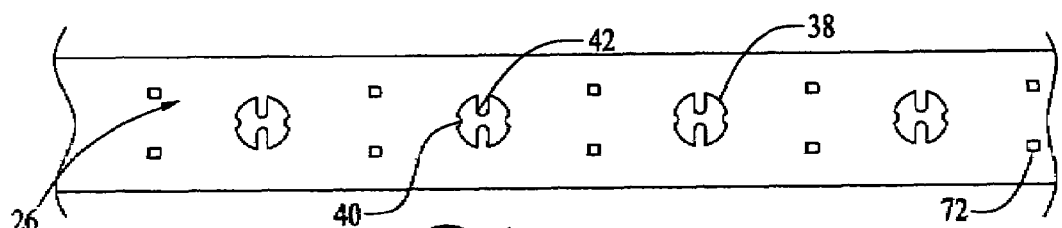
Figure 12D:
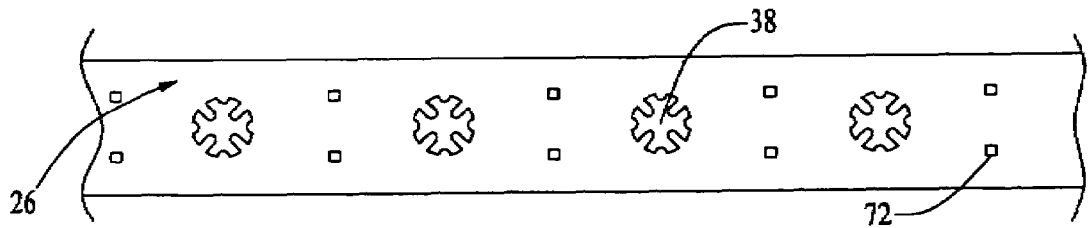

A particular embodiment illustrated in the drawings includes a hole 38 in the band with two lobes 40 extending outward from the edge of the band 26 partly across the opening of the hole 38 and two tabs 42 extending into the hole and downward from the surface. FIG. 11 is a bottom perspective view of a portion of the band or moveable strip 26 showing the tabs 42. Examples of alternative designs are shown in FIG. 12a-12d where a row of snowflake shaped openings are shown stamped or chemically etched into the band 26. In FIG. 12b one of the holes 38 is shown in its initial form (circled portion I) while another hole 38 (circled portions II of FIG. 12b demonstrates the bent down tabs 42 with inward extending lobes 40. FIG. 11c shows the embodiment of FIGS. 10 and 11. FIG. 12a shows an example of leaf spring structures 44 cut from the edge of the hole 38. The leaf spring structures 44 have a portion attached to the edge of the hole and one or two ends extending across the opening of the hole 38 to provide a spring-like grip against the side of the head 36 of the fastener 22. One skilled in the art will recognize that numerous different structures can be provided to grip the head 36 of the fastener 22.

Referring back to FIGS. 4, the tail 23 on the band 26, with fasteners 22 attached to the band, extends into the cartridge 20 and through a tensioning means 46 within the cartridge. Alternatively, the tail 23 can be attached to a reel or spool which includes a tensioning spring (not shown). The band then passes over first and second guide rollers 48, 50 and behind guiding pins 52 which extend from the inner wall 54 of the cartridge 20 over the edge of the strip 26, but not far enough to contact the fasteners 20. The forward-most fastener 22 is positioned in front of the cylinder tip 30 and the leading end 24 of the strip 26 is passed under and is engaged with the trigger 32 so that when the trigger 32 retracts during use the band is moved forward placing the next available fastener 22 in position on the cylinder tip 30.

Figure 29:
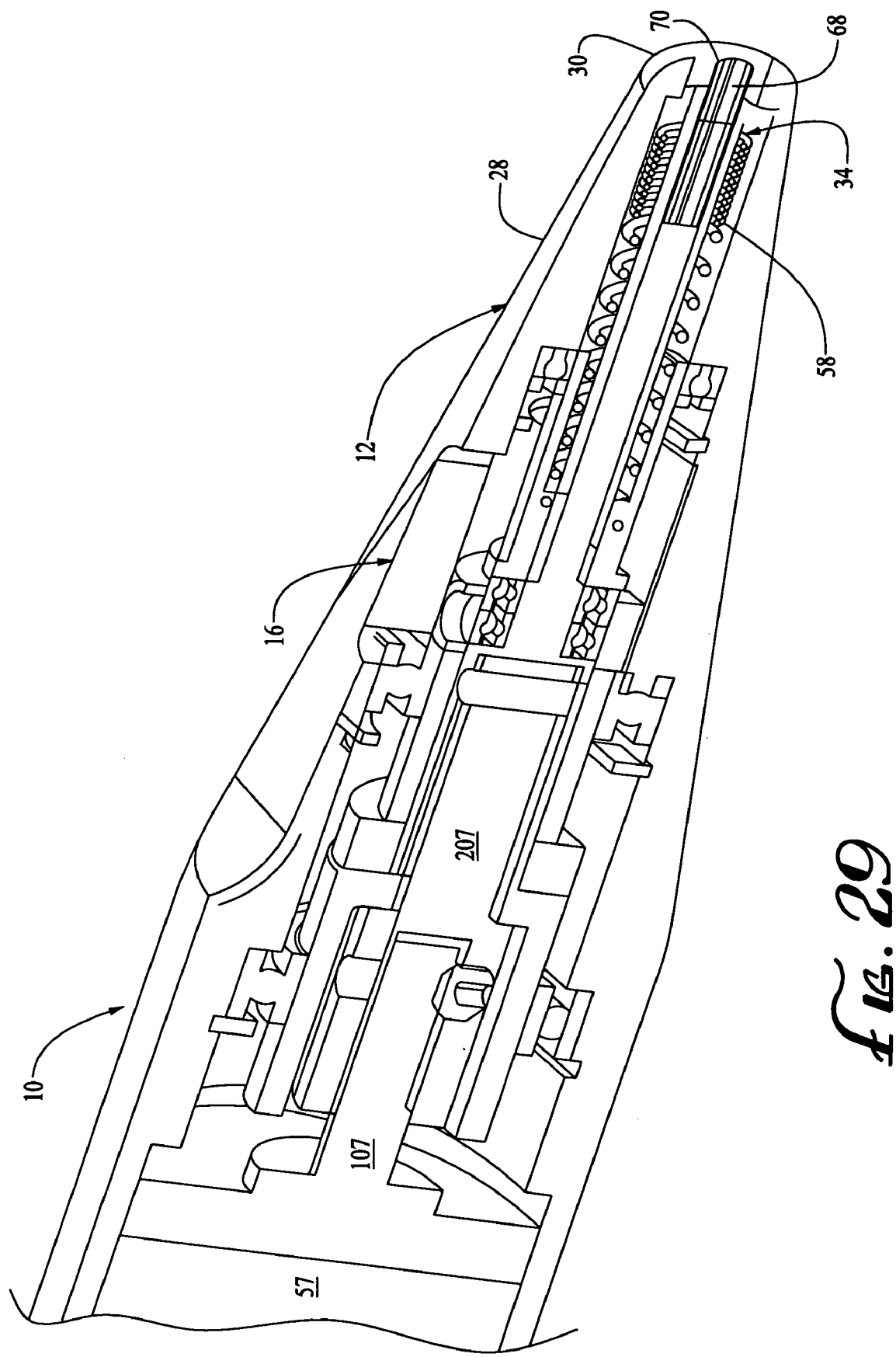
FIG. 29 is a longitudinal cross section view of the drive portion of the fastener placement system of FIG. 1.

FIG. 1 is a perspective side view and FIG. 29 is a longitudinal cross-sectional view of an embodiment of the fastener placement system 10 showing the driver assembly 14 within the screw delivery portion 12. Included within the screw delivery portion 12 is a power source, preferably a rechargeable or replaceable battery 56 which drives a motor 57, gear box 107 and drive transmission coupling 207 which in turn provides rotary motion to the driver tip 34. The motor 57 and gear assembly can include a reversing means so the tip can be rotated to insert or remove the fastener from the target bone surface. Also included are means for operatively connecting the trigger 32 on the cylinder 16 so that moving the trigger forward (toward the tip 34) also moves the driver tip 34 forward. When the trigger 32 is released a spring mechanism 58 causes the driver tip 34 to retract and, at the same time advance the strip 26, positioning the next fastener 22 for use. A separate spring (not shown) causes the pin 68 to retract.

FIGS. 5-7 show a preferred embodiment of the fastener 22 for use with the fastener placement system 10. The threaded portion 60 is similar to that on threaded fasteners currently used for medical applications. The head 36 of the fastener 22 has a recessed surface 62 which includes two radially spaced holes 64 extending perpendicular to the recessed surface 62. These holes are sized to receive two like-sized and shaped driver pins 68 which extend from and retract into the driver tip 34. While the driver pins 68 are preferably sized and shaped like the holes, they can be of any shape as long as they fit in the holes. Also, the holes 64 do not have to be round but can be of any shape and in fact can each be a different shape. The wall of the head 36 of the fastener 22 extending above the recessed surface 62 has a taper 66 extending inwardly from the top down, as best shown in FIG. 6a. FIGS. 8 and 9 show a similar shaped outwardly extending portion or flange 70 on the driver tip 34. The flange 70, being slightly larger then the top of the taper 66, allows the driver tip 34 to be inserted into the head of the fastener 22 and grasp the fastener head 36, interlocking with the head 36 of the fastener 22, as shown in FIG. 30 to separate the fastener from the strip 26.

To use the fastener placement system 10 a loaded cartridge 20 is slid into track 21 on the lower wall of the cylindrical shell 16, the moveable strip 26 is placed over the front portion 28 and across the tip 30. A first fastener 22 is positioned extending outward from the tip 30. The leading edge 24 is fed under the trigger 32. The trigger 32 is manually advanced toward the tip 30, which causes power from the battery 56 to be delivered to the motor 57, causing the tip 34 to rotate and to move forward toward the fastener head 36. Continued forward movement causes the flange 70 to enter the head of the fastener and interlock with the taper 66 while at the same time the driver pins 68 are extended into the holes 64 in the head of the fastener 22. Substantially simultaneously with the flange 70 and taper 66 grasping each other and the pins 68 entering the holes 64 the fastener 22 becomes detached from the strip 26. The driver tip 34, with the rotating fastener 22 attached thereto, now extends through the mounting hole 38 and the rotating fastener 22 can be applied to the bone surface for securing the bone pieces together. Releasing the trigger 32 allows spring 58 to exert rearward motion on the driver tip 34. The separate springs (not shown) also cause the pins 68 to retract, the driver tip 34 to separate from the fastener head 36 and the rotation of the driver tip 34 to cease. As the trigger moves back to its resting position extensions on the bottom of the trigger (not shown) set into drive holes 72 spaced along the edge of the band 26, grasping the band and causing the leading edge 24 to move rearward, which positions the next fastener 22 in front of the cylinder tip 30 and driver tip 34 so that the above described action can be repeated.

While the above described embodiment describes two pins 68 that insert into holes 64 in the fastener head 36 one or more geometric shaped holes or slots in the head of the fastener 22, and matching structure on the driver tip 34 can be used to accomplish the same screw placement function. Alternative interacting hole or holes 64 and driver tip 34 include numerous common structures used on the head of screws and bolts including but not limited to Phillips head, Allen wrench, slots and other geometric shapes as shown in FIGS. 12-21a. FIGS. 13-16 show some alternative designs for the fastener head structure. While FIG. 7 shows a circular top inner edge on the recess, other non-circular or modified circular designs may be used. FIGS. 13-16a and b are top and cross-sectional views of four alternatives. FIGS. 16a and b show a fastener 34 with a round, serrated edge 67 to aid in grasping the fastener for rotation. FIG. 13a and b show an upper inner edge with six sides, but other geometric shapes can be used. FIGS. 14 and 15 show rounded variations of the design of FIG. 13.

Figure 22:
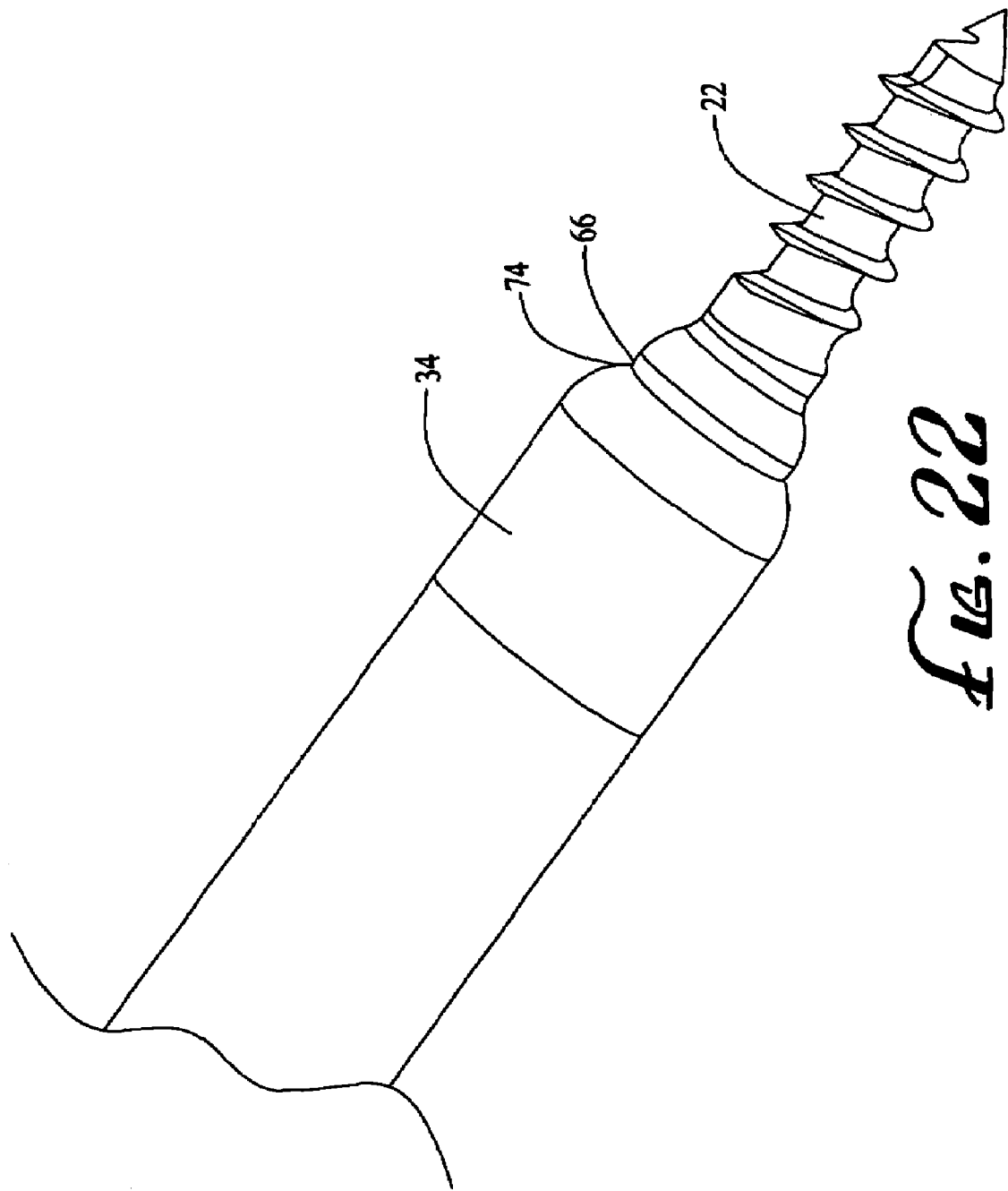
FIG. 22 is a perspective side view of a driver tip holding one of the embodiments of FIGS. 17-21.
Figure 27:
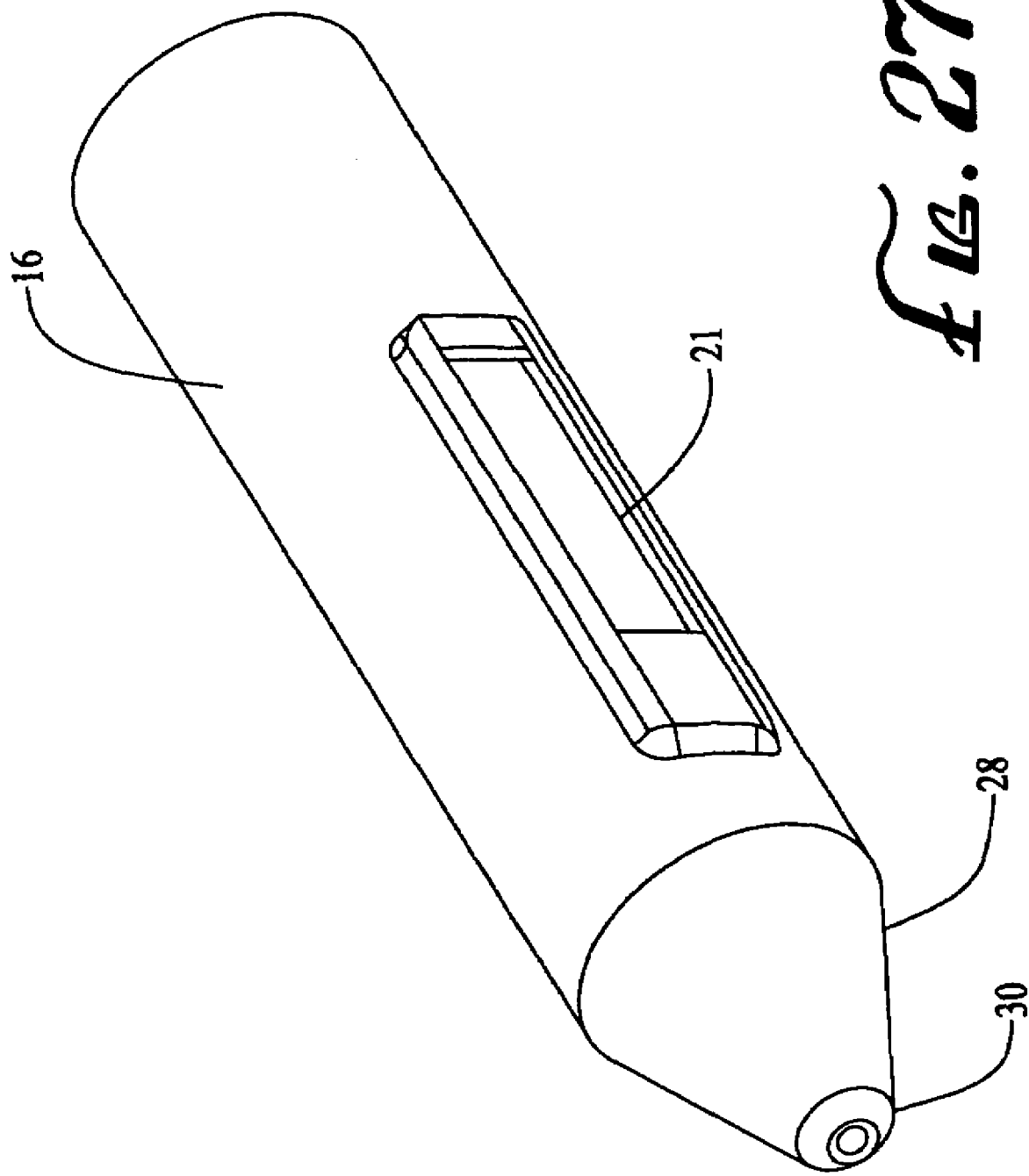
FIG. 27 is a bottom perspective side view of the screw delivery portion showing the track for mounting the replaceable cartridge assembly.
Figure 28:
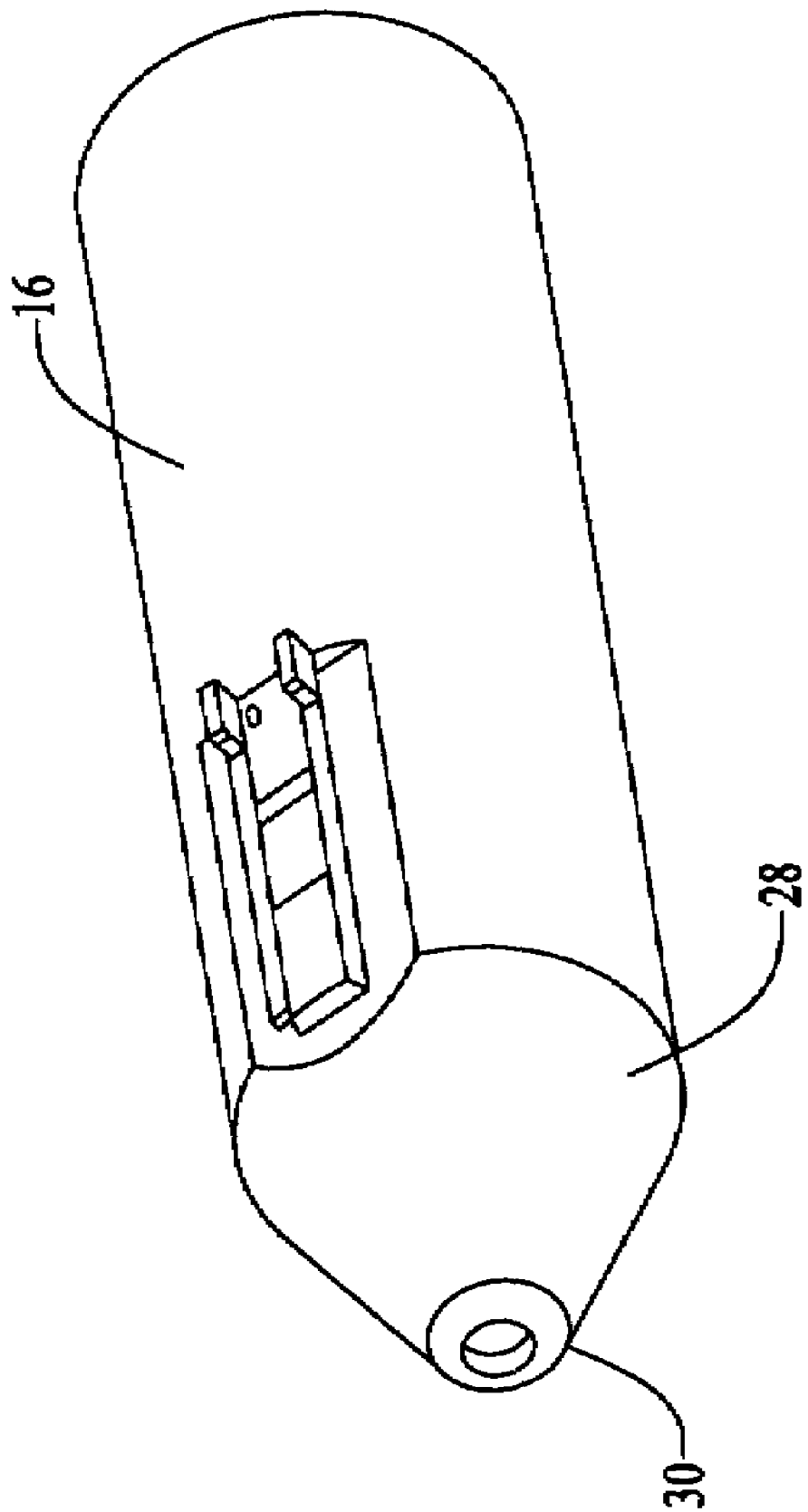
FIG. 28 is a top perspective view of the screw delivery portion showing the tape receiving rack with the advancement trigger removed.

FIGS. 17-21a, b and c show top, cross sectional and side views of five alternative embodiments with different shaped hole 64 structures in the head 36 of the fastener 22. As best shown in FIGS. 17-21c, these fasteners 22 also have a taper 66 on the outer surface of the head 32 which can be grabbed by inwardly extending portion 74 on a driver tip 34 as shown in FIG. 22. FIGS. 23-26a and b are top and longitudinal cutaway views of still further embodiments which show extensions 76 from the head 36 of the fastener. The driver pins 68, instead of sitting into holes 64 in the head 36 of the fastener 22 are structured to grasp or surround the extensions 76. One skilled in the art will recognize that a combination of holes 64 and extensions 76 can also be used.

Figure 31:
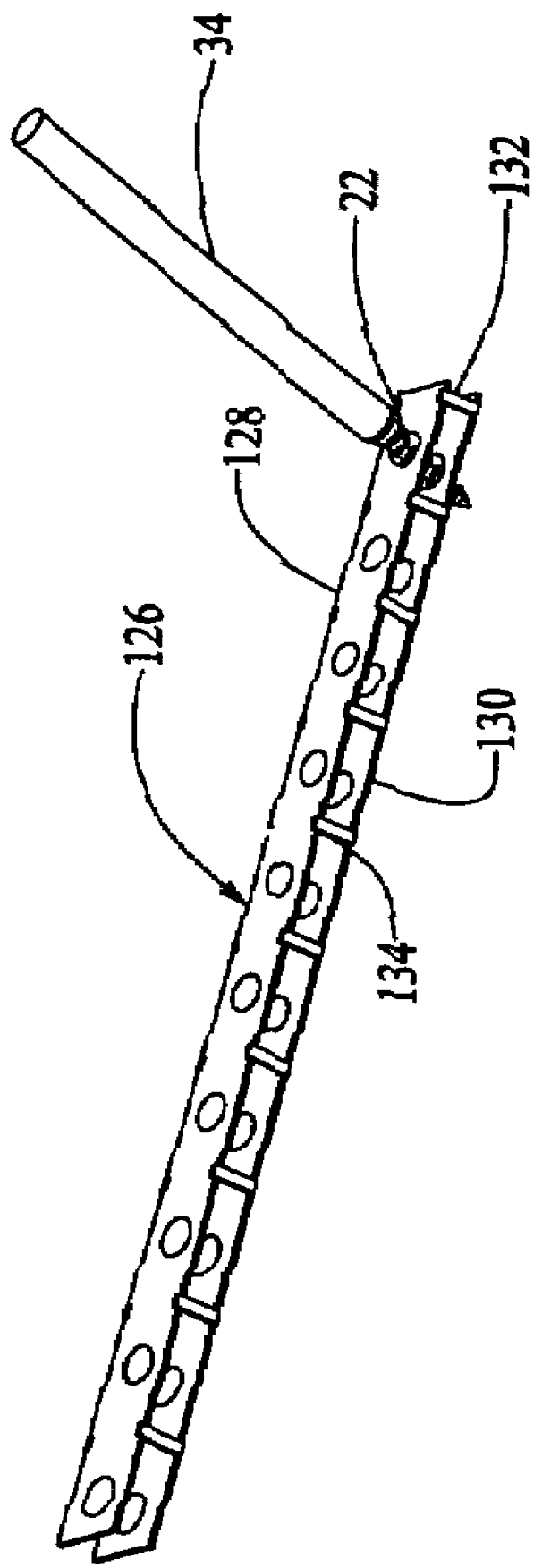
FIG. 31 is a perspective view of an alternative band structure for holding the fasteners.

FIG. 31 shows an alternative band 126 which has an upper band 128, which holds the fastener 22 in a manner as described above, and a lower band 130 to aid in aligning the fastener. The lower band 130 also has holes there through which have a diameter greater than the head 36 of the fastener 22 so the fastener will pass through without bending. Also shown is the driver tip (with the cylindrical shell 16 not shown). The upper band 128 and lower band 130 are connected by posts 132. To allow the two layer band to wrap around curves, the lower band 130 has slits 134 across the width.

I claim:

1. A device for automatically feeding a series of medical fasteners to a location for mating with a rotary fastener driver and for placement of each of said series of medical fasteners into tissue or bone structure to hold said tissue or bone structure together, comprising:

a driver body, a powered screw driver positioned within the driver body, a fastener carrier system removable from and attachable to the driver body and means for positioning and advancing the individual fasteners of the series of medical fasteners in a controlled manner to a position to receive a driving tip on the powered screw driver, the medical fastener comprising a screw having a head with a recess therein for receiving the tip of the screw driver, the head of the screw and the tip of the screw driver having interlocking structures such that, once the tip is inserted in the recess in the screw head the screw is carried by the driver tip until intentionally dislodged, the recess further including one or more structures therein or thereon which interact with mating structures on the driver tip to transmit rotary motion of the driver tip to the screw, wherein the recess in the screw head has a depth suitable to receive the tip of the screw driver, an inner side wall extending from an upper edge of the recess to a lower edge of the recess, at least a portion of the inner side wall having a peripheral length greater then the length of the periphery of the upper edge, the tip of the screw driver having an enlargement thereon, the tip configured so that the enlargement can be pushed into the recess in the screw head and lodge within said portion of the inner wall.

2. The device of claim 1 wherein the fastener carrier system comprises an elongated band, the band having a leading end, a trailing end and central fastener retaining portion, the central fastener retaining portion having holes equally spaced along the length thereof on a central longitudinal axis, a fastener located in each of said holes and held in the hole by contacting means extending from the edges of the hole inwardly and in contact with the outer surface of the side wall of the head of the fastener.

3. The device of claim 2 wherein the contacting means comprise one or more lobes extending from the inner edge of the hole extending parallel to the upper surface of the band, one or more spring-like extensions attached to the inner edge of the hole, or one or more tabs extending from the inner edge of the hole substantially perpendicular to the upper surface of the band.

4. The device of claim 1 wherein the portion of the inner side wall tapers outwardly from the upper edge of the recess.

5. The device of claim 1 wherein the side wall of the recess has a uniform contour along its entire circumference.

6. The device of claim 1 wherein the one or more structures therein or thereon the head of the screw which interact with mating structures on the driver tip to transmit rotary motion of the driver tip to the screw comprises one or more holes in the base of the recess for receiving one or more like shaped structures or pins on, extending or extendable from the screw driver tip.

7. The device of claim 6 wherein the one or more holes comprise one or more star shaped indents, one or more slots, or one or more geometric shapes in the base of the recess.

8. A device for automatically feeding a series of medical fasteners to a location for mating with a rotary fastener driver and for placement of each of said series of medical fasteners into tissue or bone structure to hold said tissue or bone structure together, comprising:

a driver body, a powered screw driver positioned within the driver body, a fastener carrier system removable from and attachable to the driver body and means for positioning and advancing the individual fasteners of the series of medical fasteners in a controlled manner to a position to receive a driving tip on the powered screw driver, the medical fastener comprising a screw having a head with a recess therein for receiving the tip of the screw driver, the head of the screw and the tip of the screw driver having interlocking structures such that, once the tip is inserted in the recess in the screw head the screw is carried by the driver tip until intentionally dislodged, the recess further including one or more structures therein or thereon which interact with mating structures on the driver tip to transmit rotary motion of the driver tip to the screw, wherein the means for positioning and advancing the individual fasteners of the series of medical fasteners in a controlled manner to a position to receive a driving tip on the powered screw driver comprises a finger actuated trigger mounted on the driver body, a) movement of said finger actuated trigger to a driving position extends the tip of the screw driver to interlock said tip with the head of the fastener, removes the fastener from the fastener carrier system and causes rotary motion to be applied to the fastener for driving the fastener into the bone structure, and b) release of the trigger or movement of the trigger to an off position following positioning of the fastener in the bone disconnects the screw driver tip from the fastener head, retracts the screw driver tip from the fastener carrier system and causes the fastener carrier system to advance forward, to position a subsequent fastener in a position to be grasped by the screw driver tip.

9. A device for feeding a series of medical fasteners to a location for mating with a rotary fastener driver and for placement of each of said series of medical fasteners into tissue or bone structure to hold said tissue or bone structure together, comprising:

an assembly including a powered screw driver and a fastener carrier mounted external thereto, the fastener carrier including, or adapted to receive, a series of individual medical fasteners on a moveable band to provide and position said individual fasteners of the series of medical fasteners in a controlled manner to a position to receive a driving tip on the powered screw driver, the medical fastener comprising a screw having a head with securing structure therein or thereon interacting with the tip of the screw driver such that, once the tip is placed in contact with the screw head the screw is carried by the driver tip until intentionally dislodged, the head further including one or more driving structures therein or thereon which interact with mating structures on the driver tip to transmit rotary motion of the driver tip to the screw, wherein the screw head has a recess therein with a depth suitable to receive the tip of the screw driver, an inner side wall extending from an upper edge of the recess to a lower edge of the recess, at least a portion of the inner side wall having a peripheral length greater then the length of the periphery of the upper edge, the tip of the screw driver having an enlargement thereon, the tip configured so that the enlargement can be pushed into the recess in the screw head and lodge within said portion of the inner wall.

10. The device of claim 9 wherein the moveable band comprises an elongated band having a leading end, a trailing end and central fastener retaining portion, the central fastener retaining portion having holes equally spaced along the length thereof on a central longitudinal axis, a fastener located in each of said holes and held in the hole by contacting means extending from the edges of the hole inwardly and in contact with the outer surface of a side wall of the head of the fastener.

11. The device of claim 10 wherein the contacting means comprise one or more first extensions extending from the inner edge of the hole parallel to the upper surface of the band and one or more second extensions attached to the inner edge of the hole extending in a direction other then parallel to the upper surface.

12. The device of claim 11 wherein the one or more second extensions from the inner edge of the hole are substantially perpendicular to the upper surface of the band.

13. The device of claim 9 wherein the portion of the inner side wall tapers outwardly from the upper edge of the recess.

14. The device of claim 9 wherein the driving structure therein or thereon which interacts with mating structures on the driver tip to transmit rotary motion of the driver tip to the screw comprises a side wall shape on the screw head, one or more holes in the base of a recess in the screw head for receiving one or more complementary shaped structures or pins on, extending or extendable from the screw driver tip or one or more extensions from the head of the fastener to be received by complementary structure on the screw driver tip.

15. The device of claim 14 wherein the one or more driving structures comprise one or more star shaped indents or extensions, one or more slots or elongated extensions, or one or more holes or extension with a defined shaped periphery in or on the head of the fastener, the screw driver having a complementary mating structure for driving the head of the screw in a rotary manner.

16. The device of claim 9 further including a trigger mechanism which interacts with the moveable band to place a fastener in a position to be grasped by the driving tip, activation of the trigger causing rotary motion to be applied to the fastener to separate the fastener from the band and drive the fastener into the bone.

17. An assembly for placing a fastener in a bone or removing a fastener from a bone comprising a powered screw driver and individual medical fasteners, the driver having a configuration designed to interact with the head of the fastener such that the head of the fastener is grasped by the driver tip, the medical fastener comprising a screw having a head with securing structure therein or thereon interacting with the tip of the screw driver such that, once the tip is placed in contact with the screw head, the screw is carried by the driver tip until intentionally dislodged, the head further including one or more driving structures therein or thereon which interact with mating structures on the driver tip, said mating structures on the driver tip transmitting rotary motion of the driver tip to the screw, wherein the screw head has a recess therein with a depth suitable to receive the tip of the screw driver, an inner side wall extending from an upper edge of the recess to a lower edge of the recess, at least a portion of the inner side wall having a peripheral length greater then the length of the periphery of the upper edge, the tip of the screw driver having an enlargement thereon, the tip configured so that the enlargement can be pushed into the recess in the screw head and lodged within said portion of the inner wall.

18. The device of claim 17 wherein the portion of the inner side wall tapers outwardly from the upper edge of the recess.

19. The device of claim 17 wherein the one or more driving structures therein or thereon which interact with mating structures on the driver tip to transmit rotary motion of the driver tip to the screw comprise a side wall shape on the head of the screw, one or more holes in a base of a recess in the head for receiving one or more complementary shaped structures or pins on, extending or extendable from the screw driver tip or one or more extensions from the head of the fastener to be received by complementary structure on the screw driver tip.

20. The device of claim 19 wherein the one or more structures comprise one or more star shaped indents or extensions, one or more slots or elongated extensions, or one or more holes or extension with a defined shaped periphery in or on the head of the fastener, the screw driver having a complementary structure for driving the head of the screw in a rotary manner.

* * * * *

UNITED STATES PATENT AND TRADEMARK OFFICE
CERTIFICATE OF CORRECTION

| | | |
|---|---|---|
| PATENT NO. | : 7,406,899 B2 | Page 1 of 1 |
| APPLICATION NO. | : 11/506489 | |
| DATED | : August 5, 2008 | |
| INVENTOR(S) | : Douglas W. Walker | |

It is certified that error appears in the above-identified patent and that said Letters Patent is hereby corrected as shown below:

Patent Title Page Item (76) Inventor:

On Title Page, column 1, inventor of patent, correct to Douglas [[D.]] --W.-- Walker Signed and Sealed this Thirtieth Day of December, 2008

JON W. DUDAS
*Director of the United States Patent and Trademark Office*